US00PP37513P2

(12) United States Plant Patent
Nannes

(10) Patent No.: US PP37,513 P2
(45) Date of Patent: Jul. 7, 2026

(54) ***ECHEVERIA* PLANT NAMED 'BINL-77120083'**

(50) Latin Name: ***Echeveria* spp.**
Varietal Denomination: BINL-77120083

(71) Applicant: Botanical Innovation B.V., Wageningen (NL)

(72) Inventor: Jacobus A.M. Nannes, Nairobi (KY)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 19/344,923

(22) Filed: Sep. 30, 2025

(51) Int. Cl.
*A01H 6/32* (2018.01)
*A01H 5/12* (2018.01)

(52) U.S. Cl.
USPC ..... Plt./373

(58) Field of Classification Search
USPC ..... Plt./373
CPC ..... A01H 6/32; A01H 5/12
See application file for complete search history.

*Primary Examiner* — Keith O. Robinson

(57) ABSTRACT

A new and distinct cultivar of *Echeveria* plant named 'BINL-77120083' is disclosed, characterized by flattened rosettes with intense bronze-colored leaf-tips and fully bronze young leaves in the heart/center of the plant. The new cultivar is an *Echeveria*, typically used as an ornamental plant.

2 Drawing Sheets

Figure 1:
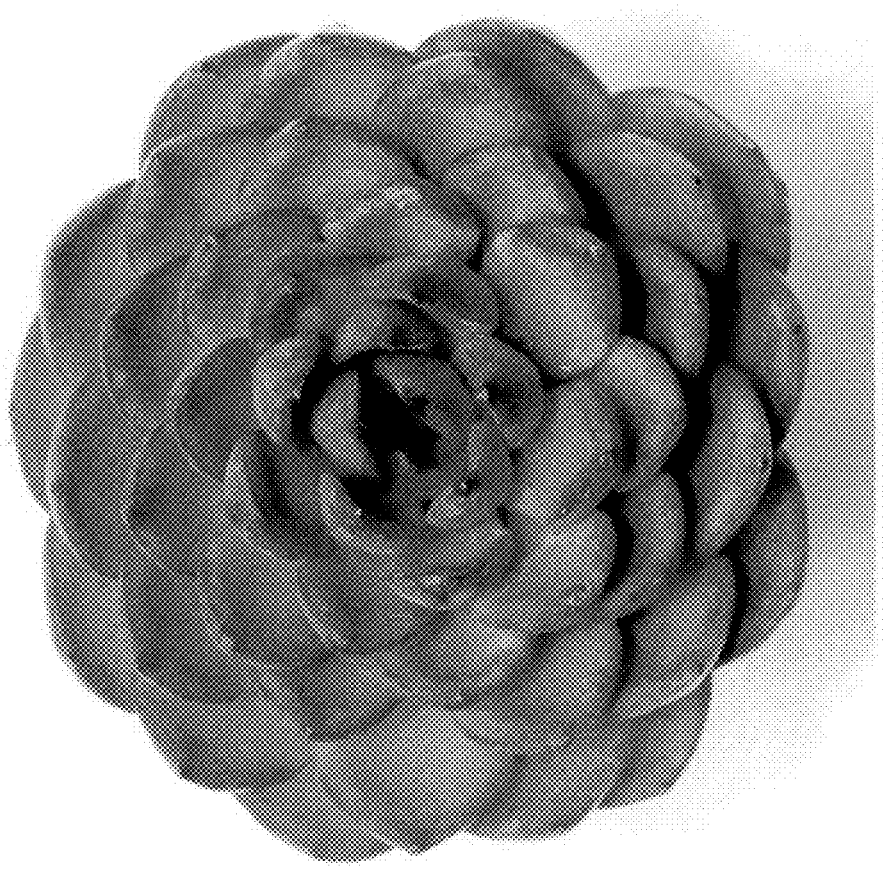

Latin name of the genus and species: *Echeveria* spp.
Cultivar denomination: 'BINL-77120083'.

BACKGROUND OF THE INVENTION

The new cultivar is a product of a planned breeding program to produce distinct and better performing *Echeveria* cultivars. The new cultivar is the result of a crossing made by the inventor in May of 2019. The seed parent is the unpatented *Echeveria* 'Christmas'. The pollen parent is the unpatented *Echeveria* 'Nina'. The new cultivar was selected by the inventor in August of 2020 at a nursery in Nairobi, Kenya.

Asexual reproduction of the new cultivar 'BINL-77120083' by terminal cuttings was first performed at the same nursery in Nairobi, Kenya in August of 2020, and has shown that the unique features of this cultivar are stable and reproduced true to type through successive generations.

SUMMARY OF THE INVENTION

The cultivar 'BINL-77120083' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77120083'. These characteristics in combination distinguish 'BINL-77120083' as a new and distinct *Echeveria* cultivar:

1. Intense bronze apical marginal flushing of the older leaves and fully bronze young leaves in the heart/center of the rosette-shaped plant.
2. Thick leaves, hence not stretching easily or quickly.
3. Compact rosette-like plant-shape.

PARENT COMPARISONS

Plants of the new cultivar 'BINL-77120083' are similar to plants of the female parent in most horticultural characteristics, however, plants of the new cultivar 'BINL-77120083' differ from in the following characteristics:

1. Leaf color of the new cultivar is intense bronze on the leaf-tips with of the older leaves with fully bronze young leaves in the heart/center. Leaf color of the seed parent is light green with a small/narrow red leaf-rim/edge at the top of the leaves.
2. Plants of the new cultivar have a less upright growth habit than plants of the seed parent.

Plants of the new cultivar 'BINL-77120083' are similar to plants of the male parent in most horticultural characteristics, however, plants of the new cultivar 'BINL-77120083' differ in the following characteristics:

1. Leaf color of the new cultivar is intense bronze on the leaf-tips with of the older leaves with fully bronze young leaves in the heart/center. Leaf color of the pollen parent is more evenly colored, with younger leaves fully pinkish-red, older leaves turn to a more red and green color.
2. Leaf aspices are more rounded than leaf aspices of the pollen parent.

COMMERCIAL COMPARISONS

Plants of the new cultivar 'BINL-77120083' are similar to plants of the unpatented commercial cultivar *Echeveria agavoides*, the species itself. However, plants of the new cultivar differ in the following characteristics:

1. Leaf color of the new cultivar is intense bronze on the leaf-tips with of the older leaves and more full red young leaves in the heart/center. Leaf color of this comparator is light green with a small/narrow red-brown leaf-rim at the top of the leaf.

Plants of the new cultivar 'BINL-77120083' are similar to plants of the commercial cultivar *Echeveria* 'Spotlight', unpatented. However, plants of the new cultivar differ in the following characteristics:

1. Leaf color of the new cultivar is intense bronze on the leaf-tips with of the older leaves fully bronze young leaves in the heart/center. Leaf color of this comparator is green with red tips.

BRIEF DESCRIPTION OF THE PHOTOGRAPHS

The accompanying photograph in FIG. 1 illustrates in full color a top-down view of a typical plant of 'BINL-77120083' grown in a greenhouse. The plant is approximately 24 weeks of age.

Figure 2:
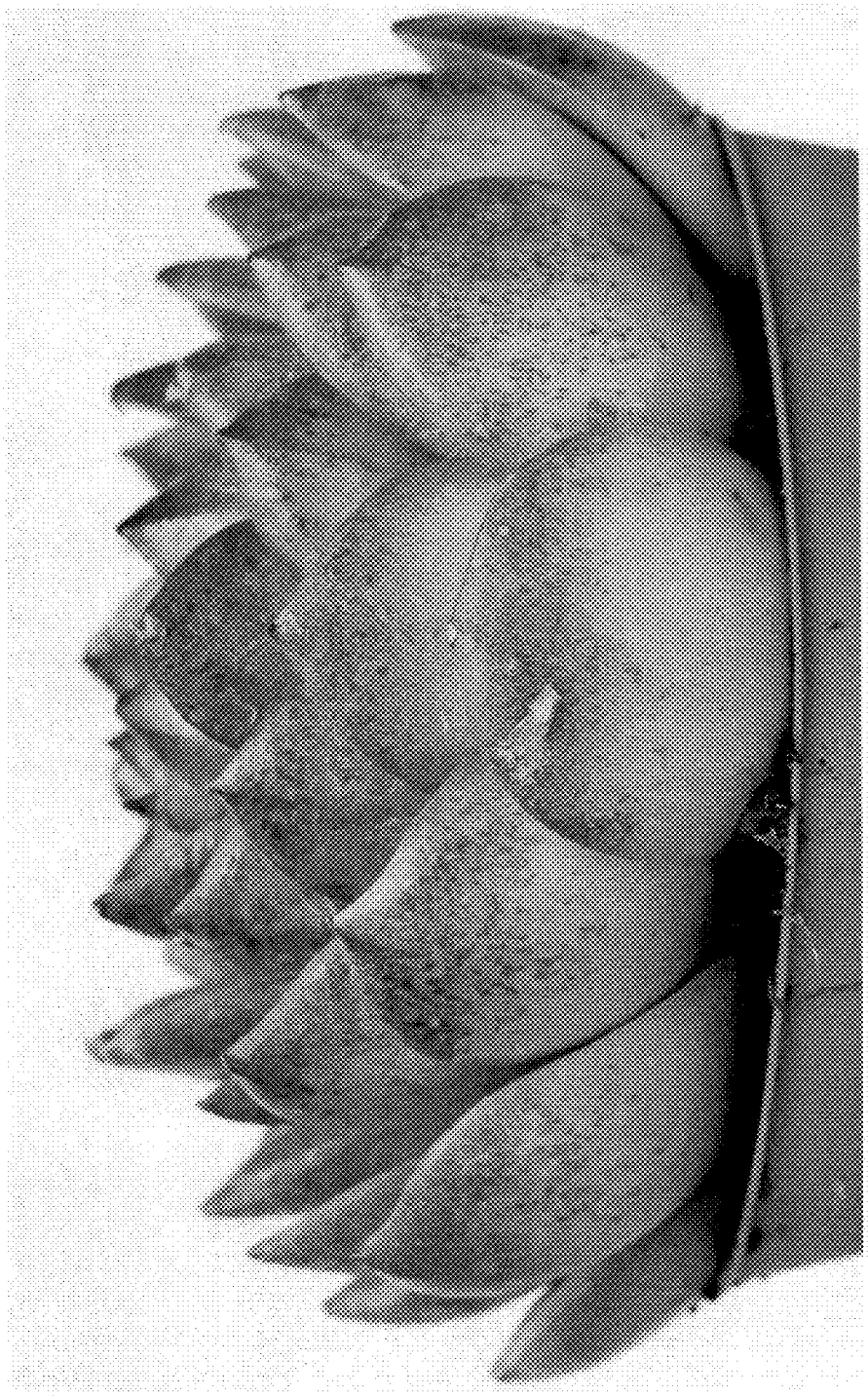

FIG. 2 is a side-view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-77120083' plants at 24 weeks of age, grown in a greenhouse in Nairobi, Kenya during August. The growing temperature ranged from 12° C. to 20° C. at night to 20° C. to 28° C. during the day. Measurements and numerical values represent averages of typical flowering types.

Botanical classification: *Echeveria* spp. 'BINL-77120083'.

PROPAGATION

Time to initiate roots: About 14 days in summer, 21 days in winter at approximately 20° C.

Time to produce rooted cutting: About 45 days in summer, 60 days in winter at approximately 20° C.

Description of roots: Thin, herbaceous, moderately dense, freely branching. White in color, not accurately measured with R.H.S. chart.

PLANT

Plant type: Tender succulent perennial.

Plant shape: Flattened (basal rosette).

Growth habit: Basal rosette of leaves.

Plant spread: Average 12.4 cm.

Height: Average 6.7 cm.

Age of plant described: Approximately 24 weeks.

Branching habit: Leaves in basal rosettes, no main stems or lateral stems present.

Pinching: Pinching not required.

FOLIAGE

Leaf:

*Arrangement*.—Single rosette.

*Quantity*.—Average 55 per rosette.

*Average length*.—6.3 cm.

*Average width*.—3.3 cm.

*Shape*.—Obovate to broad oblong-obovate.

*Aspect*.—Moderately to slightly concave, leaves in an average angle of 50° to horizontal (=0°).

*Apex*.—Broad apiculate to abruptly acute. Base: Cuneate.

*Margin*.—Entire.

*Texture*.—Top surface: Glabrous, smooth. Bottom surface: Glabrous, smooth.

*Pubescence*.—None; both sides glabrous.

*Luster, upper side*.—Slightly glossy.

*Luster, under side*.—Slightly glossy.

*Rugosity, upper side*.—Non-rugose.

*Rugosity, under side*.—Non-rugose.

*Color*.—Young foliage upper side: Greyed-Green 197A completely tinted Brown 200A, margin Greyed-Purple 187C. Base Yellow-Green 147D. Young foliage under side: Greyed-Purple N186C towards the top, fading to Greyish-Yellow-Green 195B towards the base. Mature foliage upper side: Yellow-Green 147C. Margin Greyed-Purple 184B, strongly tinged Greyed-Green 197A and Brown N200B towards the apex, Greyed-Red 178A at the base. Mature foliage under side: Yellow-Green 147C, fading to 147D towards the base, strongly tinged Brown 200B, 200C and 200D at the top, Greyed-Red 178A at the base.

*Venation*.—Pattern: No veins visible.

*Other*.—Leaves succulent, average thickness: 9.5 mm.

OTHER CHARACTERISTICS

Flower: Not observed to date.

Seeds and fruits: None observed to date.

Disease/pest resistance: Neither resistance nor susceptibility to normal diseases and pests of *Echeveria* has been observed.

Temperature tolerance: Tolerates temperatures up to 40° C. Hardy to USDA zones 11 to 13. Moderate tolerance to rain. High tolerance to wind.

What is claimed is:

1. A new and distinct cultivar of *Echeveria* plant named 'BINL-77120083' as herein illustrated and described.

* * * * *